United States Patent [19]

Schrader et al.

[11] Patent Number: 5,089,257
[45] Date of Patent: Feb. 18, 1992

[54] PREPARATION FOR THE SIMULTANEOUS COLORING, WASHING, AND CONDITIONING OF HUMAN HAIR

[75] Inventors: Dieter Schrader, Duesseldorf; Peter Flemming, Oberhausen-Sterkrade, both of Fed. Rep. of Germany

[73] Assignee: Henkel Kommanditgesellschaft auf Aktien, Duesseldorf-Holthausen, Fed. Rep. of Germany

[21] Appl. No.: 408,986

[22] Filed: Sep. 18, 1989

Related U.S. Application Data

[63] Continuation-in-part of Ser. No. 745,599, Jun. 17, 1985, abandoned, which is a continuation of Ser. No. 581,662, Feb. 21, 1984, abandoned, which is a continuation of Ser. No. 288,768, Jul. 31, 1981, abandoned.

[51] Int. Cl.$^5$ .......................... A61K 7/075; A61K 7/13
[52] U.S. Cl. .................................. 424/70; 424/DIG. 3; 8/408; 8/409; 8/410; 8/412; 8/416; 8/421; 8/423
[58] Field of Search ............... 8/408, 428; 424/70, 424/DIG. 3

[56] References Cited

U.S. PATENT DOCUMENTS 4,171,203 10/1979 Rose et al. ........................ 8/10.2

Primary Examiner—Thurman K. Page
Assistant Examiner—Amy Hulina
Attorney, Agent, or Firm—Ernest G. Szoke; Wayne C. Jaeschke; William H. Dippert

[57] ABSTRACT

This invention relates to a hair dye preparation. More specifically, this invention relates to a preparation for the simultaneous coloring, washing, and conditioning of human hair which consisting essentially of a mixture of:
(a) a coupler-developer oxidation coloring agent;
(b) a cationic polymer;
(c) an anionic surfactant;
(d) an amphoteric surfactant; and
(e) conventional cosmetic aids selected from the group consisting of direct dyestuffs, wetting agents, thickeners, perfumes, and water.

6 Claims, No Drawings

PREPARATION FOR THE SIMULTANEOUS COLORING, WASHING, AND CONDITIONING OF HUMAN HAIR

RELATED APPLICATIONS

This application is a continuation-in-part of U.S. patent application Ser. No. 745,99, abandoned filed June 17, 1985, which in turn is a continuation of U.S. patent application Ser. No. 581,662, abandoned filed Feb. 21, 1984, which in turn is a continuation of U.S. patent application Ser. No. 288,768 July 31, 1981.

FIELD OF THE INVENTION

This invention relates to a hair dye preparation. More specifically, this invention relates to an oxidation dye-based preparation useful in the simultaneous coloring, washing, and conditioning of human hair.

BACKGROUND OF THE INVENTION

It is known that hair dyed or tinted by means of oxidation dyes has no luster without special after-treatment, feels hard, and is difficult to comb. To eliminate these inconveniences, it has already been suggested to impart to hair dyed or tinted by means of hair coloring agents based upon oxidation dyes and washed separately, the previous luster, fullness, and combability in a subsequent separate treatment with rinses based on cationic products. In German published patent application (DE-AS) No. P 26 51 749.7 it has already been suggested to reduce these required three steps of the hair treatment, that is, dyeing/-tinting, washing, and conditioning, to two steps. According to this reference, the hair is first treated with a special hair coloring agent consisting of an oxidation dye composition and a cationic polymer and is subsequently washed with a special shampoo which contains at least one anionic surfactant and, preferably, also a cationic polymer.

U.S. Pat. No. 4,240,450 is directed to compositions for the treatment of keratin material wherein the composition comprises a combination of a cationic polymer with an anionic polymer to cause the anionic polymer to be retained on hair. This patent teaches that an anionic polymer must be present. Also, none of the compositions disclosed are suitable for the simultaneous coloring, washing, and conditioning of hair.

OBJECTS OF THE INVENTION

It is an object of the invention to provide a hair dye preparation based upon oxidation hair dyes.

It is also an object of the invention to provide a hair dye composition useful for the simultaneous coloring, washing, and conditioning of human hair.

It is a further object of the invention to provide a hair dye preparation comprising a mixture of (a) an oxidation coloring agent; (b) a cationic polymer; (c) an anionic surfactant; and (d) an amphoteric surfactant.

It is a yet further object of the invention to provide an aqueous preparation for the simultaneous coloring, washing, and conditioning of human hair after addition of oxidation agent, which consists essentially of:

(a) from about 0.02 to 5 percent by weight, based upon the total weight of the preparation, of coupler-developer oxidation coloring agent comprising at least one coupler selected from the group consisting of resorcinol, 2-methylresorcinol, α-naphthol, 2,7-dihydroxynaphthalene, pyrocathechin, hydroquinone, 1,5-dihydroxy-naphthalene, m-phenylenediamine and derivatives thereof, m-amino-phenyl, m-tolulene-diamine, 2,4-diaminoanisole, and 2,6-diaminopyridine and at least one developer selected from the group consisting of p-phenylene diamine, p-toluylene diamine, o-phenylene diamine, o-toluylene diamine, p-aminophenol, p-aminodiphenylamine, o-aminophenyl, 2,4,5,6-tetraaminopyrimidine, 4-aminopyrazolone derivatives, and heterocyclic hydrazones;

(b) from about 0.5 to 4 percent by weight, based upon the total weight of the preparation, of the reaction product of hydroxyethyl cellulose with the reaction product of equimolar amounts of epichlorohydrin and trimethylamine per substituted anhydroglucose unit;

(c) from about 1 to 25 percent by weight, based upon the total weight of the preparation, of an anionic surfactant of the sulfonate, sulfate, or synthetic carboxylate type selected from the group consisting of alkylbenzene sulfonates ($C_{9-15}$-alkyl); mixtures of alkene and hydroxyalkene sulfonates; esters of α-sulfofatty acids; sulfuric acid monoesters of primary and secondary alcohols; sulfated fatty acid alkanolamides; sulfated fatty acid-monoglycerides; sulfated reaction products of 1 to 4 mols of ethylene oxide with primary or secondary fatty alcohols or alkyl phenols; fatty acid esters or fatty acid amides of hydroxycarboxylic acids, aminocarboxylic acids, or aminosulfonic acids; and fatty alcohol ether sulfates of the formula $$R-O-(CH_2CH_2O)_nCH_2CH_2OSO_3Me \qquad (II)$$

wherein R represents an alkyl of from about 10 to 16 carbon atoms, n is an integer of from 1 to 3, and Me represents a salt-forming base; and (d) from about 1 to 5 percent by weight, based upon the total weight of the preparation, of an amphoteric or zwitterionic surfactant containing both acid groups, selected from the group consisting of carboxyl, sulfo, sulfuric half ester, phosphono, and phosphonic acid ester groups, and basic groups, selected from the group consisting of amino, imino, ammonium, quaternary ammonium, quaternary phosphonium, and tertiary sulfonium compounds, the weight ratio of component (c) to component (d) being from about 5:1 to 1:1, in the absence of an anionic polymer, as well as a method of using same.

These and other objects of the invention will become more apparent from the discussion below.

DETAILED DESCRIPTION OF THE INVENTION

It has been found that coloring, that is, dyeing or tinting, washing, and conditioning of human hair can be effected in one operation, that is, one step, with a preparation according to the invention. The preparation consists essentially of a mixture of (a) a coupler-developer oxidation coloring agent; (b) a cationic polymer; (c) an anionic surfactant; (d) an amphoteric surfctant; and (e) conventional cosmetic aids selected from the group consisting of direct dyestuffs, wetting agents, thickeners, perfumes, and water, preferably in the absence of an anionic polymer.

The oxidation dyes in component (a) useful according to the invention are aromatic compounds which are condensed by oxidants to form the dyeing compounds. These dyeing compounds comprise coupler-developer combinations, wherein the developer and coupler substances can be any of those substances presently known to be useful in this regard. Useful developer substances include, for example, p-phenylene diamine, p-toluylene diamine, o-phenylene diamine, o-toluylene diamine, p-aminophenol, p-aminodiphenylamine, o-aminophenyl, 2,4,5,6-tetraaminopyrimidine, 4-aminopyrazolone derivatives, and heterocyclic hydrazones, and useful coupler substances include, for example, resorcinol, 2-methylresorcinol, α-naphthol, 2,7-dihydroxynaphthalene, pyrocatechin, hydroquinone, 1,5-dihydroxynaphthalene, m-phenylenediamine and its derivatives, m-aminophenyl, m-toluylenediamine, 2,4-diaminoanisole, and 2,6-diaminopyridine. Additional coupler and developer substances useful according to the invention can be found, for example, in U.S. Pat. Nos. 4,171,203, 4,213,758, and Re. 30,199, all of which are incorporated herein by reference.

The concentration of the coupler-developer combination in the dye preparation according to the invention is from about 0.0 to 5 percent by weight, based on the total weight of the dye preparation.

The cationic polymers (b) to be used in the preparations according to the invention are products having diverse structures, which have in common the presence of a plurality of quaternary nitrogen atoms. A particularly versatile group of compounds comprises the quaternary cellulose ether derivatives as they are described in U.S. Pat. No. 3,472,840, incorporated herein by reference. The compounds can be produced according to the methods described in U.S. Pat. No. 3,472,840 by etherification and quaternization in any order or simultaneously. These are compounds which are formed, for example, by the reaction of hydroxyethyl cellulose with the reaction product of equimolar amounts, preferably 0.7 mol, of epichlorohydrin and trimethylamine per substituted anhydroglucose unit. Commercial products falling into this group of quaternary cellulose ether derivatives include the products JR 400, JR 30 M, and JR 125, available from Union Carbide. Of particular importance among the quaternary cellulose derivatives is the product JR 400, which yields the best results in terms of easy combability, luster, and fullness of the treated hair.

Other suitable cationic polymers for use in the preparations according to the invention are polymers containing ring structures of the formula

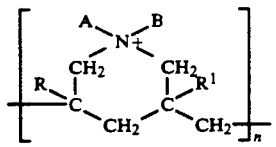 (I)

wherein
A and B independently represent a member selected from the class consisting of alkyl and phenyl radicals on which any substituents are selected from the group consisting of hydroxy, amido, carboloweralkoxy, loweralkoxy, phenoxy, naphthoxy, cyano, thioloweralkoxy, thiophenoxy, lower alkoyl, 5- and 6-membered cycloalkyl, tri-(loweralkyl)ammoniumloweralkyl, with, on the alkyl groupings only, a nitro group, and on the phenyl radicals only, a halogen atom; or, taken together, A and B represents a member selected from the group consisting of —CH₂—CH₂—, —CH(CH₃)—CH(CH₃)—,
—CH=CH—CH=CH—,
—CH=CH—CH=N—, and
—CH=CH—N=CH—;

R and R¹ independently represent a member selected from the class consisting of hydrogen, chloro, bromo, loweralkyl, and phenyl radicals; and n is an integer representing the number of units in the molecular chain, as are described in U.S. Pat. No. 3,288,770, incorporated herein by reference. In addition, other known quaternized polymers, such as those described in U.S. Pat. Nos. 4,217,914, 4,197,865, and 4,175,572, all of which are incorporated herein by reference, can be used.

The cationic polymers (b) are used in the preparations according to the invention in amounts of from about 0.5 to 4 percent by weight, based upon the weight of the total product.

Suitable anionic surfactants (c) are those of the type of the sulfonates, sulfates, and of the synthetic carboxylates. Useful surfactants of the sulfonate type include alkylbenzene sulfonates ($C_{9-15}$-alkyl) and mixtures of alkene and hydroxyalkane sulfonates, such as disulfonates, as they are obtained, for example, from monoolefins with terminal or non-terminal double bonds by sulfonation with gaseous sulfur trioxide and subsequent alkaline or acid hydrolysis of the sulfonation products. Also suitable are alkane sulfonates which are obtained from alkanes by sulfochlorination or sulfoxidation and subsequent hydrolysis or neutralization, or bisulfite addition on olefins. Other suitable surfactants of the sulfonate type include the esters of α-sulfofatty acids, for example, the α-sulfonic acids from hydrogenated methyl or ethyl esters of coconut fatty acids, palm kernel fatty acids, or tallow fatty acids.

Suitable surfactants (c) of the sulfate type include the sulfuric acid monoesters of primary alcohols (for example, from coconut fatty alcohols, tallow fatty alcohols, or oleyl alcohol) and those of secondary alcohols. Furthermore suitable are sulfated fatty acid-alkanolamides, sulfated fatty acid-monoglycerides, and sulfated reaction products of 1 to 4 mols of ethylene oxide with primary or secondary fatty alcohols or alkyl phenols.

Other suitable anionic surfactants (c) are the fatty acid esters or fatty acid amides of hydroxycarboxylic acids, aminocarboxylic acids, or aminosulfonic acids, such as the fatty acid sarcosides, fatty acid glycolates, fatty acid lactates, fatty acid taurides, or fatty acid isethionates.

Of particular importance among the anionic surfactants are the fatty alcohol ether sulfates, particularly those of the formula R—O—(CH₂CH₂O)ₙCH₂CH₂OSO₃Me (II)

wherein R represents an alkyl of from about 10 to 16 carbon atoms, n is an integer of from 1 to 3, and Me represents a salt-forming base, such as an alkali metal or ammonium ion.

The anionic surfactants (c) can be present in the form of their sodium, potassium, and ammonium salts, as well as soluble salts of organic bases, such as mono-, di-, or triethanolamine. They are contained in the preparations of the invention in an amount of from about 1 to 25 percent by weight, based upon the weight of the total preparation.

The amphoteric, or zwitterionic, surfactants (d) to be used according to the invention contain in the molecule both acid groups, such as carboxyl, sulfo, sulfuric acid half ester, phosphono, or phosphoric acid ester groups, and basic groups, such as amino, imino, or ammonium groups. Zwitterionic compounds with a quadruple-substituted, that is, quaternary, ammonium group are called betaines, even though they have a covalently bound acid group in the molecule, and the positive and negative charges are balanced intramolecularly. In a broader sense, the correspondingly substituted quaternary phosphonium and tertiary sulfonium compounds also belong to the class of the betaines. The surface-active betaines generally have on the nitrogen atom a higher molecular aliphatic hydrocarbon radical with a hydrophobic nature and two lower alkyl radicals with from 1 to 3 carbon atoms which are substituted by one or two hydroxyl groups, or which can be linked with each other directly or over a hetero-atom. The water-solubilizing carboxylate, sulfonate, or sulfate group is linked with the ammonium nitrogen over the fourth substituent, which consists mostly of a short-chain, aliphatic radical possibly having a double bond or a hydroxyl group. Also suitable as surfactants are those sulfonate betaines where the anionic, water-solubilizing group is linked directly with the long chain hydrophobic hydrocarbon radical which is responsible for the capillary activity. These sulfobetaines can be obtained, for example, from the sultones obtainable from $C_8$-$C_{20}$-$\alpha$-olefins with $SO_3$ and a tertiary amine with three short chain, aliphatic radicals. Typical representatives of these surface-active betaines are, for example, the compounds 3-(N-hexadecyl-N,N-dimethyl-ammonio)-propane sulfonate; 3-(N-tallowalkyl-N,N-dimethyl-ammonio)-2-hydroxypropane sulfonate; 3-(N-hexadecyl-N,N-bis-(2-hydroxy-ethyl)-ammonio)-2-hydroxypropyl sulfate; 3-(N-cocoalkyl-N,N-bis-(2,3-dihydroxypropyl)-ammonio)-propane sulfate; N-tetradecyl-N,N-dimethyl-ammonium-methylcarboxylate; and N-hexadecyl-N,N-bis-(2,3-dihydroxypropyl)-ammonium-methylcarboxylate. These surface-active betaines can be obtained, for example, by reacting the tertiary amine with the hydrophobic, long-chain, aliphatic hydrocarbon radical and the two lower alkyl or hydroxyalkyl radicals with quaternizing agents, such as 3-chloro-2-hydroxypropane sodium sulfate, 3-chloro-2-hydroxypropyl-sodium-sulfate, sodium chloroacetate or propane sultone, butane sultone, and carbyl or carboxyl sulfate.

The amphoteric surfactants (d) are contained in the preparations according to the invention in an amount of from about 1 to 5 percent by weight, based upon the weight of the total preparation. The ratio of anionic surfactants (c) to amphoteric surfactants (d) can range from about 5:1 to 1:1.

The conventional cosmetic aids (e) to be used according to the invention serve primarily to bring the preparation into a processable form, such as a cream, emulsion, gel, or simple solution, if desired. Such additives include water as well as, for example, wetting agents or emulsifiers of the anionic or nonionic type, such as alkylbenzene sulfonates, fatty acid alkanolamides, addition products of ethylene oxide onto fatty alcohols, thickeners, such as methyl cellulose, starch, higher fatty alcohols, paraffin oil, and fatty acids. These additives are used for these purposes in the usual amounts; for example, wetting agents and emulsifiers are used in concentrations of from about 0.5 to 30 percent by weight, and thickeners are used in concentrations of from about 0.1 to 25 percent by weight, each based upon the weight of the total preparation. In addition, the cosmetic aids can also comprise perfume oils and hair conditioners such as pantothenic acid and cholesterol.

The preparations according to the invention are produced in known manner by incorporation of the dye components into a base in the form of a cream, emulsion, or gel which consists of a mixture of anionic surfactant, amphoteric surfactant, cationic polymer, and the necessary wetting agents, emulsifiers, thickeners, hair conditioners perfumes, and water. If the use of a directly absorbing dye is required to obtain a desired tint, this is likewise incorporated into the base.

The oxidative coupling, that is, the development of the coloration, is preferably effected by means of chemical oxidants. Such oxidants particularly include hydrogen peroxide or its addition products on urea, malamine, and sodium borate, as well as mixtures of the hydrogen peroxide addition products with potassium peroxide disulfate.

For the treatment of the hair for the simultaneous dyeing/-tinting, washing, and conditioning, the preparation according to the invention is mixed directly before use with one of the above-mentioned oxidants. The preparation according to the invention—regardless of whether it is a cream, a solution, a gel, or an emulsion—can be used in a weakly acid, neutral, or particularly alkaline medium at a pH of from about 8 to 10. The application temperature ranges from about 15° to 40° C. After an action of from about 10 to 45 minutes, the hair is lathered with some water and subsequently rinsed clear. The hair has been dyed or tinted after this single-stage treatment in the desired shade, is easy to comb when wet, and has a luster and a good feel after drying. The advantage obtained by the use of the preparation according to the invention is that the hair is dyed or tinted, washed, and made easy to comb in a single treatment step and can be put into the original shiny, soft, easy-to-handle state.

The following examples are intended to illustrate the invention and should not be construed as limiting it thereto.

EXAMPLES

Example 1

Medium Blond Hair Dye, Simultaneous Washing and Conditioning Composition

| Component | Parts by Weight |
| --- | --- |
| $C_{12-18}$ fatty alcohol | 10.5 |
| Sodium laurylether sulfate | 5.0 |
| Cocoalkyl-dimethyl-ammonium betaine | 3.0 |
| JR 400 polymer | 1.0 |
| α-Naphthol | 0.04 |
| 1,3-Bis-(2,4-diaminophenoxy)-propane | 0.01 |
| Resorcinol | 0.15 |
| p-Toluylene-diamine sulfate | 0.21 |
| Trilon BS (ethylenediaminetetraacetic acid, available from BASF) | 0.20 |
| Sodium sulfite | 1.00 |
| Ammonia, 25% | 6.00 |
| Water | 72.89 |
| | 100.00 |

Twenty parts by weight of the above preparation were mixed directly before use with 20 parts by weight of 5% hydrogen peroxide solution. The mixture was applied on light-blonde hair. After 30 minutes, the hair was lathered with some water and subsequently rinsed clear. The hair was medium blonde after the treatment and could be easily combed in the wet state. After drying, the hair had a silky luster and a pleasant, soft and full feel.

Example 2

Copper-Gold Hair Tinting Agent, Simultaneous Washing, and Conditioning Composition

| Component | Parts by Weight |
|---|---|
| $C_{12-18}$ fatty alcohol | 10.5 |
| Sodium cocoalkylether sulfate | 5.0 |
| N-Tetradecyl-N,N-dimethyl-ammonium acetate | 3.0 |
| JR 400 polymer | 1.0 |
| 2,4,5,6-Tetraaminopyrimidine sulfate-monohydrate | 0.30 |
| 2-Methyl resorcinol | 0.075 |
| 2,7-Dihydroxynaphthalene | 0.075 |
| m-Aminophenol | 0.01 |
| Resorcinol | 0.05 |
| p-Toluylene-diamine sulfate | 0.10 |
| p-Aminophenol hydrochloride | 0.15 |
| Trilon BS (ethylenediaminetetraacetic acid, available from BASF) | 0.20 |
| Sodium sulfite | 1.00 |
| Ammonia, 25% | 6.00 |
| Water | 72.54 |
| | 100.00 |

Twenty parts by weight of the above preparation were mixed directly before use with 20 parts by weight of 6% hydrogen peroxide solution. The mixture was applied to light-blonde hair. After 20 minutes, the hair was lathered with some water and subsequently rinsed clear. The hair was copper-gold after the treatment and could be easily combed in the wet state. After drying the hair had a silky luster and a soft full feel.

Example 3

Black Hair Dye, Simultaneous Washing and Conditioning Composition

| Component | Parts by Weight |
|---|---|
| $C_{12-18}$ fatty alcohol | 10.5 |
| Sodium cocoalkylether sulfate | 5.0 |
| N-hexadecyl-N,N-bis-(2,3-dihydroxypropyl)-ammonium acetate | 3.0 |
| 1,3-Bis-(2,4-diaminophenoxy)-propane | 0.35 |
| JR 400 polymer | 1.0 |
| Resorcinol | 1.00 |
| p-Toluylenediamine sulfate | 3.00 |
| Trilon BS (ethylenediaminetetraacetic acid, available from BASF) | 0.20 |
| Sodium sulfite | 1.00 |
| Ammonia, 25% | 8.5 |
| Water | 66.45 |
| | 100.00 |

Twenty parts by weight of the above preparation were mixed directly before use with 20 parts by weight of 6% hydrogen peroxide solution. The mixture was applied on medium blonde hair. After 30 minutes, the hair was lathered with some water and subsequently rinsed clear. The hair was black after the treatment and could be easily combed in the wet state. After drying, the hair had a silky luster and a soft and full feel.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An aqueous preparation for the simultaneous coloring, washing, and conditioning of human hair after addition of oxidizing agent, which consists essentially of:
   (a) from about 0.02 to 5 percent by weight, based upon the total weight of the preparation, of coupler-developer oxidation coloring agent comprising at least one coupler selected from the group consisting of resorcinol, 2-methylresorcinol, α-naphthol, 2,7-dihydroxynaphthalene, pyrocatechin, hydroquinone, 1,5-dihydroxynaphthalene, m-phenylenediamine and derivatives thereof, m-amino-phenyl, m-tolulene-diamine, 2,4-diaminoanisole, and 2,6-diaminopyridine and at least one developer selected from the group consisting of p-phenylene diamine, p-toluylene diamine, o-phenylene diamine, o-toluylene diamine, p-aminophenol, p-aminodiphenylamine, o-aminophenyl, 2,4,5,6-tetraamino-pyrimidine, 4-aminopyrazolone derivatives, and heterocyclic hydrazones;
   (b) from about 0.5 to 4 percent by weight, based upon the total weight of the preparation, of the reaction product of hydroxyethyl cellulose with the reaction product of equimolar amounts of epichlorohydrin and trimethylamine per substituted anhydroglucose unit;
   (c) from about 1 to 25 percent by weight, based upon the total weight of the preparation, of an anionic surfactant of the sulfonate, sulfate, or synthetic carboxylate type selected from the group consisting of alkylbenzene sulfonates ($C_{9-15}$-alkyl); mixtures of alkene and hydroxyalkene sulfonates; esters of α-sulfofatty acids; sulfuric acid monoesters of primary and secondary alcohols; sulfated fatty acid alkanolamides; sulfated fatty acid-monoglycerides; sulfated reaction products of 1 to 4 mols of ethylene oxide with primary or secondary fatty alcohols or alkyl phenols; fatty acid esters or fatty acid amides of hydroxycarboxylic acids, aminocarboxylic acids, or aminosulfonic acids; and fatty alcohol ether sulfates of the formula $$R-O-(CH_2CH_2O)_nCH_2CH_2OSO_3Me \qquad (II)$$

wherein R represents an alkyl of from about 10 to 16 carbon atoms, n is an integer of from 1 to 3, and Me represents a salt-forming base; and
   (d) from about 1 to 5 percent by weight, based upon the total weight of the preparation, of an amphoteric or zwitterionic surfactant containing both acid groups, selected from the group consisting of carboxyl, sulfo, sulfuric half ester, phosphono, and phosphonic acid ester groups, and basic groups, selected from the group consisting of amino, imino, ammonium, quaternary ammonium, quaternary phosphonium, and tertiary sulfonium compounds, the weight ratio of component (c) to component (d) being from about 5:1 to 1:1, no anionic polymer being present.

2. The preparation of claim 1 in the form of a cream, emulsion, gel, or solution.

3. The preparation of claim 1, wherein component (b) comprises a quaternary cellulose derivative.

4. The preparation of claim 1, wherein the amphoteric surfactant of component (d) is selected from the group consisting of 3-(N-hexadecyl-N,N-dimethyl-ammonio)-2-propane sulfonate; 3-(N-tallowalkyl-N,N-dimethyl-ammonio)-2-hydroxypropane sulfonate; 3-(N-hexadecyl-N,N-bis-(2-hydroxyethyl)-ammonio)-2-hydroxypropyl sulfate; 3-(N-cocoalkyl-N,N-bis-(2,3-dihydroxypropyl)-ammonio)-propane sulfonate; N-tetradecyl-N,N-dimethyl-ammonium-methyl-carboxylate; and N-hexadecyl-N,N-bis-(2,3-dihydroxypropyl)ammonium-methylcarboxylate.

5. A method of simultaneously coloring, washing, and conditioning human hair which comprises the steps of:
   (a) admixing the preparation of claim 1 with an oxidizing agent; and
   (b) applying an effective amount of the admixture from step (a) to said hair at a temperature of from about 15° to 40° C. for a time sufficient to effect dyeing.

6. The method of claim 5, wherein said preparation also contains a chemical oxidizing agent.

* * * * *

UNITED STATES PATENT AND TRADEMARK OFFICE
CERTIFICATE OF CORRECTION

PATENT NO. : 5,089,257
DATED : February 18, 1992
INVENTOR(S) : Schrader, et al.

It is certified that error appears in the above-identified patent and that said Letters Patent is hereby corrected as shown below:

On the title page, item [63], line 1, "Ser. No. 745,599" should read -- Ser. No. 745,999 --.

Signed and Sealed this

Thirty-first Day of August, 1993

*Attest:*

BRUCE LEHMAN

*Attesting Officer*    *Commissioner of Patents and Trademarks*